United States Patent [19]

Baumann et al.

[11] Patent Number: 5,206,390
[45] Date of Patent: Apr. 27, 1993

[54] SUBSTITUTED BISACYLOXYNAPHTHACENES

[75] Inventors: Marcus Baumann, Basel; Carl W. Mayer, Riehen, both of Switzerland; Wolfgang Wernet, Freiburg, Fed. Rep. of Germany; Walter Fischer, Reinach, Switzerland

[73] Assignee: Ciba-Geigy Corporation, Ardsley, N.Y.

[21] Appl. No.: 356,827

[22] Filed: May 24, 1989

[30] Foreign Application Priority Data

May 27, 1988 [CH] Switzerland ............ 2008/88
Jul. 19, 1988 [CH] Switzerland ............ 2754/88

[51] Int. Cl.$^5$ .................................... C07C 43/267
[52] U.S. Cl. .................... 549/214; 549/234; 552/201
[58] Field of Search ............ 560/139; 556/489; 558/427; 549/234, 214; 552/201

[56] References Cited

U.S. PATENT DOCUMENTS

2,934,544  4/1960  Cripps .................. 260/365
4,522,754  6/1985  Hilti et al. ............. 260/239

OTHER PUBLICATIONS

Bull. Soc. Chem. France (1939) 931-32.
Bull. Soc. Chem. France (1939) 1122-25.
Bull. Soc. Chem. France (1948) 418-28.
J. Chem. Res. (1981) vol. 12, p. 368.
Kametani, Tetsuji et al., "Studies on the Synthesis of Tetracycline Derivatives", (1978) Chem. Pharm. Bulletin. 26(12), pp. 3820-3824.

*Primary Examiner*—Mary C. Lee
*Assistant Examiner*—Jacqueline Haley
*Attorney, Agent, or Firm*—Kevin T. Mansfield; Edward McC. Roberts

[57] ABSTRACT

Compounds of the formula I

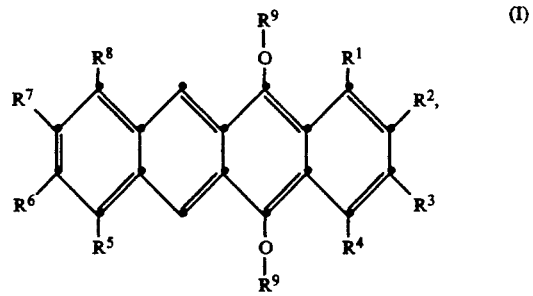

in which $R^1$ to $R^8$ independently of one another are H and at least one of $R^1$ to $R^8$ is a substituent belonging to the group —F, —Si($C_1$-$C_4$alkyl)$_3$ or —COOR$^{10}$; or each pair of adjacent radicals of $R^1$ to $R^8$ is —CO—O—CO—; or at least one of $R^1$ to $R^8$ is $C_1$-$C_{20}$alkyl—(X-)$_p$—, $C_2$-$C_{20}$alkenyl—(X)$_p$—, $C_2$-$C_{20}$-alkynyl—(X)$_p$—, $C_3$-$C_8$cycloalkyl—(X)$_p$—, ($C_1$-$C_{12}$alkyl—$C_3$-$C_8$cycloalkyl—(X)$_p$—, $C_3$-$C_8$-cycloalkyl—$CH_2$—(X)$_p$—, $C_1$-$C_{12}$alkyl—$C_3$-$C_8$cycloalkyl—$CH_2$—(X)$_p$—, $C_6$-$C_{10}$aryl—X—, $C_7$-$C_{20}$alkaryl—X—, $C_7$-$C_{12}$aralkyl—(X-)$_p$— or $C_8$-$C_{20}$—alkaralkyl—(X)$_p$— or —Y—($C_mH_{2m}$—O)—$_n$R$^{10}$ each of which is unsubstituted or substituted by —F, —OH, —CN, $C_1$-$C_{12}$alkoxy, $C_1$-$C_{12}$acyloxy or —COOR$^{10}$; $R^{10}$ is H or $C_1$-$C_{18}$alkyl, X is —O—, —S—, —SO— or —SO$_2$— and Y is —O— or —S—, and p is 0 or 1, m is a number from 2 to 6 and n is a number from 2 to 20; and $R^9$ is $C_1$-$C_4$acyl which is unsubstituted or substituted by —F. The compounds are intermediates for the preparation of 5,6,11,12-tetrathiotetracenes which form electrically conducting charge-transfer complexes with electron donors.

8 Claims, No Drawings

SUBSTITUTED BISACYLOXYNAPHTHACENES

The invention relates to 5,12-acyloxynaphthacenes which are substituted in the 1-, 2-, 3-, 4-, 7-, 8-, 9-and/or 10-positions, to a process for their preperation and to a process for the preparation of unsubstituted or correspondingly substituted 5,6,11,12-tetrathiotetracenes.

Naphthacene-5,11-diones are important intermediates in the preparation of tetrathiotetracenes and tetraselenotetracenes. Depending on the reaction conditions and the reaction time, the reduction of the diones gives dihydrotetracenes, tetracenes or mixtures thereof. The tetracenes can be chlorinated to give 5,11-dichlorotetracenes or 6,12-dichlorotetracenes.

The direct reaction of dihydrotetracene with sulfur gives tetrathiotetracene in moderate yields [Ch. Marschalk, Bull. Soc. Chim. France pages 931 and 1122 (1939)]. The direct reaction of tetracenes and dichlorotetracenes with sulfur also gives tetrathiotetracenes [EP-A 0,153,905 and Ch. Marschalk, Bull. Soc. Chim. France, page 427 (1948)]. The preparation of tetrathiotetracenes of maximum purity by these processes requires, inter alia, that pure tetracenes be used as the starting materials. The reduction of naphthacenediones, however, often gives mixtures with hydroxytetracenes and dihydroxytetracenes, and, in addition, the yields are not satisfactory. In addition, hydroxytetracenes and dihydroxytetracenes do not react with sulfur to give tetrathiotetracenes.

5,12-Diacetoxytetracene has been described by T. Kametani in Chem. Pharm. Bull. 26(12), pages 3820-3824 (1978).

It has now been found that 5,12-diacyloxytetracenes can be reacted directly with sulfur to give 5,6,11,12-tetrathiotetracenes. The 5,12-diacyloxytetracenes are accessible in this reaction in high yields and high states of purity by simple reductive acylation.

The invention relates to compounds of the formula I

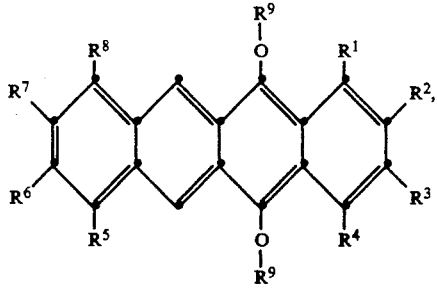

(I)

in which $R^1$ to $R^8$ independently of one another are H and at least one of $R^1$ to $R^8$ is a substituent belonging to the group —F, —Si($C_1$-$C_4$alkyl)$_3$ or —COOR$^{10}$; or each pair of adjacent radicals of $R^1$ to $R^8$ is —CO—O—CO—; or at least one of $R^1$ to $R^8$ is $C_1$-$C_{20}$alkyl—(X-)$_p$—, $C_2$-$C_{20}$alkenyl—(X)$_p$—, $C_2$-$C_{20}$alkynyl—(X)$_p$—, $C_3$-$C_8$cycloalkyl—(X)$_p$—, ($C_1$-$C_{12}$alkyl—$C_3$-$C_8$cycloalkyl—(X)$_p$—, $C_3$-$C_8$—cycloalkyl—CH$_2$—(X)$_p$—, $C_1$-$C_{12}$alkyl—$C_3$-$C_8$cycloalkyl—CH$_2$—(X)$_p$—, $C_6$-$C_{10}$aryl—X—, $C_7$-$C_{20}$alkaryl—X—, $C_7$-$C_{12}$aralkyl—(X-)$_p$— or $C_8$-$C_{20}$alkaralkyl—(X)$_p$— or —Y—($C_m$H$_{2m}$—O)—$_n$R$^{10}$ each of which is unsubstituted or substituted by —F, —OH, —CN, $C_1$-$C_{12}$alkoxy, $C_1$-$C_{12}$acyloxy or —COOR$^{10}$; $R^{10}$ is H or $C_1$-$C_{18}$alkyl, X is —O—, —S—, —SO— or —SO$_2$— and Y is —O— or —S—, and p is 0 or 1, m is a number from 2 to 6 and n is a number from 2 to 20; and $R^9$ is $C_1$-$C_4$acyl which is unsubstituted or substituted by —F.

Where $R^1$ to $R^8$ are —Si($C_1$-$C_4$alkyl)$_3$, the alkyl group can be methyl, ethyl, n-propyl, isopropyl, n-butyl and isobutyl. —Si(CH$_3$)$_3$ is particularly preferred.

Where $R^1$ to $R^8$ are —COOR$^{10}$, $R^{10}$ can be linear or branched alkyl preferbly having 1 to 12 C atoms and particularly having 1 to 8 C atoms. Examples of alkyl are methyl, ethyl and the isomers of propyl, butyl, pentyl, hexyl, heptyl, octyl, nonyl, decyl, undecyl, dodecyl, tetradecyl, hexadecyl and octadecyl.

Within the scope of the preceding definitions, $R^1$ to $R^8$ can be substituted, preferably monosubstituted to trisubstituted and particularly monosubstituted or disubstituted. Examples of suitable substituents are linear or branched alkoxy preferably having 1 to 6 C atoms and particularly having 1 to 4 C atoms. Ethoxy and methoxy are particularly preferred.

Examples of suitable substituents are also acyloxy preferably having 1 to 6 C atoms, for example $C_1$-$C_6$alkyl—COO— or benzyloxy. Examples are formyloxy, acetoxy, trifluoroacetoxy, propionyloxy, acryloyloxy, methacryloyloxy and butanoyloxy.

The substituents can also be, for example, —COOR$^{10}$ in which $R^{10}$ is preferably H or $C_1$-$C_4$alkyl.

In a preferred embodiment, $R^1$ to $R^8$ can be substituted by —OH, —F, $C_1$-$C_4$—alkoxy, —COO—($C_1$-$C_4$alkyl) and $C_1$-$C_6$alkyl—CO—O—.

$R^1$ to $R^8$ can be $C_1$-$C_{20}$alkyl—(X)$_p$—. The alkyl group can be linear or branched and preferably contains 1 to 18, particularly 1 to 12, and especially 1 to 8, atoms. Examples of alkyl groups have been mentioned previously.

$R^1$ to $R^8$ can be $C_2$-$C_{20}$alkenyl—(X)$_p$— in which p is preferably 1, X is preferably —O— and the alkenyl group preferably contains a terminal alkene group. The alkenyl group can be linear or branched and can preferably contain 2 to 18, particularly 2 to 12, and especially 2 to 6, C atoms. Examples are ethenyl, allyl, prop-1-en-1-yl, prop-1-en-2-yl, but-1-en-1- or -2- or -3- or -4-yl, but-2-en-1-yl, but-2-en-2-yl, pent-1-en-1- or -2- or -3- or -4- or -5-yl, pent-2-en-1- or -2- or -3- or -4- or -5-yl, hex-1-en-1- or -2- or -3-or -4- or -5- or -6-yl, hex-2-en-1- or -2- or -3- or -4- or -5-or -6-yl, hex-3-en-1- or -2- or -3- or -4-or -5- or -6-yl, heptenyl, octenyl, nonenyl, decenyl, undecenyl, dodecenyl, tetradecenyl, hexadecenyl and octadecenyl.

$R^1$ to $R^8$ can be $C_2$-$C_{20}$alkynyl—(X)$_p$— in which p is preferably 1, X is preferably —O— and the alkynyl group preferably contains a terminal alkyne group. The alkynyl group can be linear or branched and preferably contains 2 to 18, particularly 2 to 12, and especially 2 to 6, C atoms. Examples are ethinyl, propargyl, but-1-yn-3-yl, but-1-yn-4-yl, pent-1-yn-3- or -4- or -5-yl, hex-1-yn-3- or -4- or -5- or -6-yl, hex-2-yn-1- or -4- or -5- or -6-yl, hex-3-yn-1-yl, hex-3-yn-2-yl, heptynyl, octynyl, nonynyl, decynyl, undecynyl and dodecynyl. $R^1$ to $R^8$ can be $C_3$-$C_8$cycloalkyl—(X)$_p$— in which p is preferably 1 and the cycloalkyl group preferably contains 3 to 6 C atoms, particularly 5 or 6 C atoms. Examples are cyclopropyl, cyclobutyl, cyclopentyl, cyclohexyl, cycloheptyl and cyclooctyl. $R^1$ to $R^8$ can be ($C_1$-$C_{12}$alkyl)—$C_3$-$C_8$cycloalkyl—(X)$_p$— in which the alkyl group preferably contains 1 to 6 C atoms, p is preferably 1 and the cycloalkyl group is preferably cyclopentyl or cyclohexyl. Examples are methylcyclopentyl, methylcyclohexyl, ethylcyclopentyl, ethylcyclohexyl, methylcyclopropyl and methylcyclobutyl.

$R^1$ to $R^8$ can be $C_3$-$C_8$cycloalkyl—$CH_2$—$(X)_p$—, preferably $C_5$—or $C_6$—cycloalkyl—$CH_2$—$(X)_p$— in which p is preferably 1.

$R^1$ to $R^8$ can be $(C_1$-$C_{12}$alkyl)—$C_3$-$C_8$cycloalkyl—$CH_2$—$(X)_p$— in which p is preferably 1, the alkyl group preferably contains 1 to 6 C atoms and the cycloalkyl group is preferably cyclopentyl or cyclohexyl. Examples are methylcyclohexylmethyl or methylcyclohexylethyl.

Where $R^1$ to $R^8$ are $C_6$-$C_{10}$aryl—X—, the aryl group is particularly naphthyl and especially phenyl. Where $R^1$ to $R^8$ are $C_7$-$C_{20}$alkaryl—X—, they are preferably $(C_1$-$C_{14}$alkyl)—phenyl—X— in which the alkyl group preferably has 1 to 8 C atoms and particularly 1 to 4 C atoms.

Where $R^1$ to $R^8$ are $C_7$-$C_{12}$aralkyl—$(X)_p$—, they are preferably benzyl—X— or phenylethyl—X—.

Where $R^1$ to $R^8$ are $C_8$-$C_{20}$alkaralkyl—$(X)_p$—, they are preferably $(C_1$-$C_{13}$alkyl)—benzyl—X— in which the alkyl group contains especially 1 to 6 C atoms. Examples are methylbenzyl—X— and ethylbenzyl—X—.

Where $R^1$ to $R^8$ are —Y—$(C_mH_{2m}$—O$)_n$—$R^{10}$, Y is preferably —O—, m is preferably 2 or 3 and n is preferably a number from 2 to 12, particularly 2 to 6, and $R^{10}$ is preferably H or $C_1$-$C_4$alkyl. The $C_mH_{2m}$ group is particularly ethylene or 1,2-propylene. $R^9$ is preferably $C_1$acyl or $C_2$acyl each of which is unsubstituted or substituted by F. Examples are butanoyl, propionyl, monofluoroacetoxy, difluoroacetoxy, formyloxy and particularly acetoxy and trifluoroacetoxy.

A preferred embodiment is constituted by compounds of the formula I in which $R^1$ to $R^8$ independently of one another are H and at least one of $R^1$ to $R^8$ is a substituent belonging to the group —F, —Si(CH$_3$)$_3$, —COO—$(C_1$-$C_{12}$alkyl), $C_1$-$C_{18}$alkyl—$(X)_p$—, $C_2$-$C_{18}$alkenyl—$(X)_p$—, $C_2$-$C_{12}$alkynyl—$(X)_p$—, $C_6$-$C_{10}$aryl—X—, $C_7$-$C_{18}$alkaryl—X—, $C_7$-$C_{10}$aralkyl—$(X)_p$—, $C_8$-$C_{18}$alkaralkyl—$(X)_p$— or —Y—$(C_mH_{2m}$—O—$)_n$—$R^{10}$ each of which is unsubstituted or substituted by —F, $C_1$-$C_6$alkoxy, $C_1$-$C_6$acyloxy or —COO—$(C_1$-$C_{12}$alkyl), $R^{10}$ is H or $C_1$-$C_6$alkyl, X is —O—, —S—, —SO— or —SO$_2$— and Y is —O— or —S—, m is 2 or 3 and n is a number from 2 to 12 and p is 0 or 1 and $R^9$ is acetyl which is unsubstituted or substituted by —F.

Another preferred embodiment is constituted by compounds of the formula I in which $R^1$ and $R^4$ to $R^8$ are H; $R^2$ is —F, —CF$_3$, —COO—$(C_1$-$C_{18}$alkyl) or $C_1$-$C_{18}$alkyl—X— which is unsubstituted or substituted by —OH, —COO—$(C_1$-$C_6$alkyl) or $C_1$-$C_6$acyloxy; —Y—(CH$_2$CH$_2$O)$_n$—$R^{10}$ in which Y is —O— or —S—, $R^{10}$ is H or $C_1$-$C_6$alkyl and n is a number from 2 to 12; $C_2$-$C_{12}$alkenyl—CH$_2$—X—; $C_2$-$C_{12}$alkynyl—CH$_2$—X—; phenyl—X—; $C_1$-$C_{12}$alkylphenyl—X—; benzyl—X—; or $C_1$-$C_{12}$alkylbenzyl—X— and R$_3$ is H or independently is the same as R$_2$, and X is —O—, —S—, —SO— or —SO$_2$—.

As a substituent, $R^1$ is particularly —CF$_3$ or —COO—$(C_1$-$C_{12}$alkyl).

Preferred embodiments are also constituted by compounds of the formula I in which a) $R^4$, $R^5$ and $R^8$ are H, or b) $R^1$, $R^4$, $R^5$ and $R^8$ are H, or c) $R^2$ and/or $R^3$ are a substituent and $R^1$ and $R^4$ to $R^8$ are H, or d) $R^6$ and/or $R^7$ are a substituent and $R^1$ to $R^5$ and $R^8$ are H.

The invention also relates to a process for the preparation of compounds of the formula I, which comprises reacting a substituted naphthacene-5,12-dione of the formula II

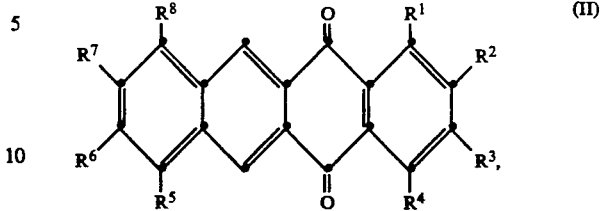

in which $R^1$ to $R^8$ are as defined above, in a solvent and under reducing conditions, with an anhydride of the formula $R^9$CO—O—OCR$^9$ in which $R^9$ is as defined above.

Reductive acylation using reducing metals, for example zinc, is known and has been described by T. Kametani in Chem. Pharm. Bull 26(12), pages 3820-3825 (1978). The reduction can also be carried out electrochemically or catalytically using noble metal catalysts, for example Pt or Pd.

The catalytic reduction or the reduction with metals is advantageously carried out in the presence of an alkali metal salt of the carboxylic acid $R^9$ COOH on which the anhydride of the formula $R^9$ CO—O—OCR$^9$ is based. The alkali metal can, for example, be Li, Na, K, Rb or Cs.

The reaction is carried out in the presence of an inert solvent, for example carboxylic acid esters, for example methyl or ethyl acetate. By this means, the reaction takes place under milder conditions and with a higher yield than in the case of the known processes.

The reaction temperature can, for example, be 20° to 100° C. It is advantageous to select a temperature within the range of room temperature, for example 20° to 40° C.

The substituted naphthacene-5,12-diones of the formula II are in part known or they can be prepared by the processes described below.

The compounds of the formula II can, for example, be prepared by carrying out a Friedel-Crafts reaction on a naphthalenedicarboxylic anhydride of the formula IV

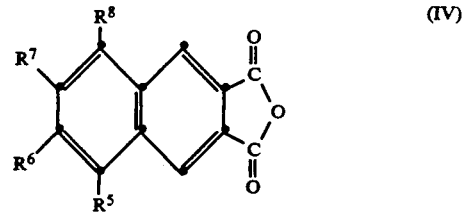

with a benzene of the formula V

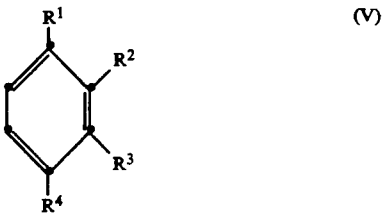

in the presence of a Lewis acid, $R^1$ to $R^8$ being as defined above, and carrying out nucleophilic substitution on compounds of the formula I in which at least one of $R^1$ to $R^8$ is —F. Compounds suitable for the nucleophilic substitution are especially those of the formula ($R^1$ to $R^8$)—X—H in which X is —O—, —S—, —SO— or —SO$_2$—, malonic acid esters or nitriles and phenylacetonitrile. These nucleophilic compounds can be used in the form of their alkali metal salts, for example, Li, Na or K salts. It is also possible to carry out the nucleophilic substitution in the presence of bases, for example solutions of alkali metal hydroxides or carbonates.

The compounds of the formula II can also be prepared by carrying out a Diels-Alder reaction on a compound of the formula VI

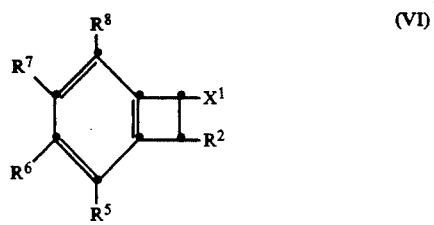

(VI)

in which $R^5$, $R^6$, $R^7$ and $R^8$ are as defined above and $X^1$ and $X^2$ independently of one another are —Cl, —Br or —I, with a compound of the formula VII

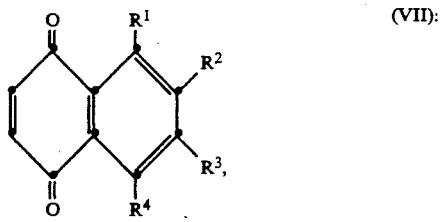

(VII):

in which $R^1$, $R^2$, $R^3$ and $R^4$ are as defined above, with subsequent elimination of $HX^1$ and $HX^2$. In the substituents $R^1$ to $R^8$, p is preferably 1.

The reaction is advantageously carried out at temperatures from 50° to 250° C., preferably 80° to 200° C. It is advantageous to use an inert solvent, for example polar, aprotic solvents. Some examples are aromatic hydrocarbons (benzene, toluene, xylene, chlorobenzene and dichlorobenzene), nitriles (actonitrile), ethers (dibutyl ether, dioxane, tetrahydrofuran, ethylene glycol dimethyl ether or diethylene glycol dimethyl ether). Isolation and purification can be carried out by customary methods, for example crystallization, sublimation or chromatography.

Compounds of the formula VI are in part known (see, for example, H. P. Cava et al., J. Am. Chem. Soc., page 1701 (1957) and J. W. Barton et al., J. Chem. Soc. Perkin Trans. 1, pages 967–971 (1986)), or can be prepared by analogous processes. The 1,2-bis-(dichloromethyl or dibromomethyl)benzenes are also in part known or can be obtained by customary electrophilic or nucleophilic substitution reactions of corresponding o-dimethylbenzenes, followed by chlorination or bromination with, for example, N-chlorosuccinimide or N-bromosuccinimide.

The p-naphthoquinones of the formula VII are known and can be obtained, for example, by nucleophilic substitution of protected or unprotected and substituted or unsubstituted halogeno-1,4-naphthoquinones or nitro-1,4-naphthoquinones with, for example, the compounds described above in the presence of alkali metal compounds ($K_2CO_3$, $CS_2CO_3$, KOH, NaOH, $NaNH_2$, $NaOCH_3$ or $NaOC_2H_5$) or with alkali metal compounds, for example those of Li, K, Na, Rb or Cs. Halogenonaphthoquinones and nitronaphthoquinones are described, for example, in Houben-Weyl, Quinones I, Volume 7/3b (1977). The naphthoquinones of the formula VII can also be prepared in a known manner by electrophilic or nucleophilic substitution of substituted or unsubstituted naphthalenes, dihydronaplthalenes or tetrahydronaphthalenes and subsequent conversion into the substituted 1,4-napthoquinones.

The compounds of the formula II can also be prepared by reacting 1,2-bis-(dihalogenomethyl)-benzenes of the formula

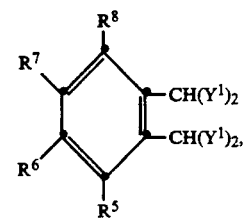

in which $Y^1$ is Cl, Br or I with a compound of the formula VII in the presence of NaI in an organic solvent. This method has been described by J. W. McOmie in Synthesis, pages 416–417 (1973).

Compounds of the formula II can also be prepared by reacting anthracene-1,4-quinones of the formula

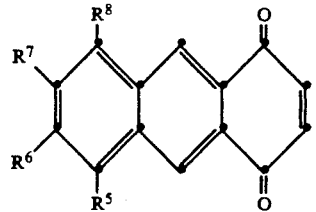

with an α-pyrone of the formula VIII

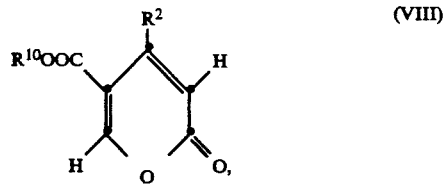

(VIII)

or with a butadiene of the formula IX

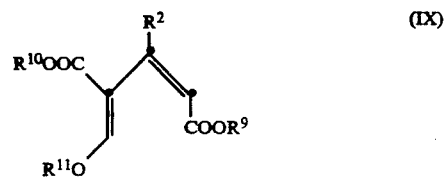

(IX)

$R^{11}$ being $C_1$–$C_6$alkyl, $R^{10}$ being as defined above and preferably being $C_1$–$C_6$alkyl. This method and the preparation of α-pyrones has been described in U.S. Pat. No. 4,617,151 and in EP-A 0,195,743.

Compounds of the formulae VIII and IX can be obtained, for example, in the following manner, X¹ being an alkali metal:

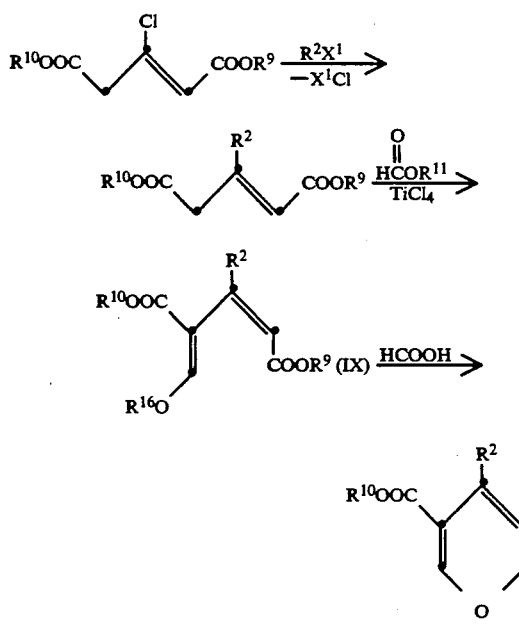

Where R¹ to R⁸ are a polyoxaalkylene radical, compounds of this type are also obtained by reacting compounds of the formula I in which R¹ to R⁸ are hydroxyalkyloxy with epoxides. It is also possible to modify the radicals R¹ to R⁸ by classic reactions, for example hydrolysis, esterification, transesterification, amidation, oxidation or reduction. Carboxylic acid esters can be converted into the trifluoromethyl derivatives in a known manner by means of HF/SF₄.

The compounds of the formula I are obtained in short reaction times in high yields and in a high state of purity. Surprisingly, they are suitable for direct reaction with sulfur with the formation of tetrathiotetracenes.

The invention also relates to a process for the preparation of 5,6,11,12-tetrathiotetracenes of the formula III

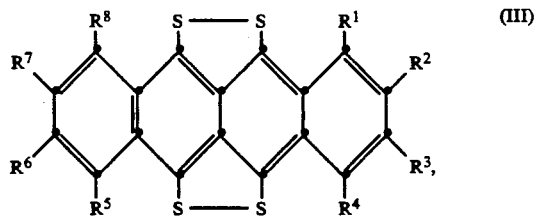

in which R¹ to R⁸ independently of one another are H or a substituent belonging to the group —F, —Si(C₁-C₄alkyl)₃ or —COOR¹⁰; or each pair adjacent radicals of R¹ to R⁸ is —CO—O—CO—; or R¹ to R⁸ are a substituent belonging to the group C₁-C₂₀alkyl—(X)$_p$—, C₃-C₈cycloalkyl—(X)$_p$—, C₁-C₁₂alkyl—C₃-C₈cycloalkyl—(X)$_p$—, C₃-C₈cycloalkyl—CH₂—(X)$_p$—, C₁-C₁₂alkyl—C₃-C₈cycloalkyl—CH₂—(X)$_p$—, C₆-C₁₀aryl—X—, C₇-C₂₀alkaryl—X—, C₇-C₁₂aralkyl—(X)$_p$— or C₈-C₂₀alkaralkyl—(X)$_p$— or —Y—(C$_m$H$_{2m}$—O)$_n$—R¹⁰ each of which is unsubstituted or substituted by —F, —OH, C₁-C₁₂alkoxy, C₁-C₁₂acyloxy or —COOR¹⁰; R¹⁰ is H or C₁-C₁₈alkyl, X is —O—, —S—, —SO— or —SO₂— and Y is —O— or —S—, and p is 0 or 1, m is a number from 2 to 6 and n is a number from 2 to 20; which comprises reacting a compound of the formula Ia

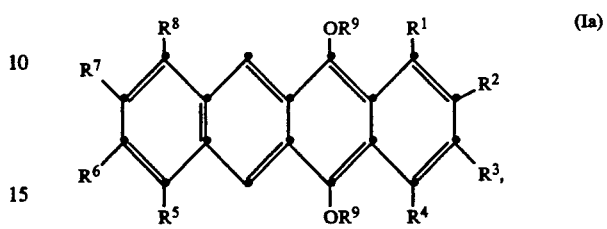

in which R¹ to R⁸ are as defined above and R⁹ is C₁-C₄acyl which is unsubstituted or substituted by —F, with sulfur in the presence of catalytic amounts of a sulfonic acid.

The reaction is advantageously carried out in a high-boiling solvent. Suitable solvents are, in particular, halogenated aromatic hydrocarbons, for example chlorobenzene, dichlorobenzenes and trichlorobenzenes, but also nitrobenzene or Dowtherm A.

The reaction is also advantageously carried out under an inert gas atmosphere, for example using noble gases (helium, neon or argon) or nitrogen.

The reaction temperature is advantageously 100° to 250° C., especially 150° to 250° C. It is advantageous to carry out the reaction at the reflux temperature of the solvent selected.

The amount of sulfonic acid can be 0.001 to 10 mol %, preferably 0.001 to 5 mol % and especially 0.01 to 2 mol %, relative to the amount of the compounds of the formula Ia.

Examples of suitable sulfonic acids are organic sulfonic acids, particularly aromatic sulfonic acids. Examples are methanesulfonic, ethanesulfonic, propanesulfonic, butanesulfonic, hexanesulfonic, trifluoromethanesulfonic or benzenesulfonic acid and especially p-toluenesulfonic acid.

The tetrathiotetracenes of the formula III are obtained in good yields by means of the process according to the invention. After being isolated, they can be purified by means of customary methods, for example by recrystallization or sublimation. In general, isolation is effected by removing the solvent, washing the residue with a non-solvent and drying.

Electrically conducting charge-transfer complexes (CT complexes) can be prepared from the compounds of the formula III by means of electron acceptors. They can be attached to polymers by means of their functional substituents, for example incorporated into polymers as side groups (cf. U.S. Pat. No. 4,617,151). The CT complexes are also suitable for the preparation of, for example, antistatic coatings of photographic film elements, magnetic tapes, electrophotographic film elements and electronic components (see U.S. Pat. No. 3,634,336). The chalcogenated tetracenes also exhibit electrochromic properties; they can be used for electrochromic displays. They are also suitable for use as laser-optical data storage units [Nach. Chem. Techn. Lab. 35, pages 255 et seq. (1987)] and as an anode material in organic solid state batteries (EP-A 0,090,598). CT complexes of substituted tetrathiotetracenes or tetraselenotetracenes can also be incorporated into thermoplastic, thermosetting or elastomeric polymers in order to achieve antistatic properties. This is effected advantageously, for example, by dissolving the substituted tetrathiotetracenes or tetraselenotetracenes, together with a soluble polymer or a precursor thereof and an electron acceptor, for example an agent which forms halogen (organic halogenated compounds, for example bromoform, trichlorobromomethane, tetrabromomethane, hexachloropropane, perchlorobutadiene, 1,3-dichloro-2-butene, 1,4-dichloro-2-butene, 1,4-bis-(trichloromethyl)-benzene, iodoacetonitrile, iodoform, tetrachloroethylene, perchlorocyclobutadiene, N-chlorosuccinimide, N-bromosuccinimide or N-iodosuccinimide), if appropriate together with a further inert solvent, and removing by evaporation at an elevated temperature the agent which forms halogen and the solvent. The resulting composition contains a network of needle-shaped crystals of the CT complex in divided form is concomitantly used, since substituted tetrathiotetracenes or tetraselenotetracenes of this type have no tendency, or only a slight tendency, to crystallize in the polymer.

The following examples illustrate the invention in greater detail.

A) PREPARATION EXAMPLES

Examples 1-22

31.05 mmol of zinc powder are added with stirring to 10.35 mmole of 2-substituted naphthacene-5,12-dione, 40 ml of ethyl acetate, 25 ml of acetic anhydride and 31.05 mmol of potassium acetate. After being stirred for 40 minutes at 25° C., the reaction mixture is filtered and the residue is washed four times with $CH_2Cl_2$. The filtrates are evaporated and the residue is recrystallized from $CH_2Cl_2$/pentane and then from toluene. The yields and melting points of the 2-substituted 5,12-diacetoxynaphthacenes obtained are shown in Table 1.

TABLE 1

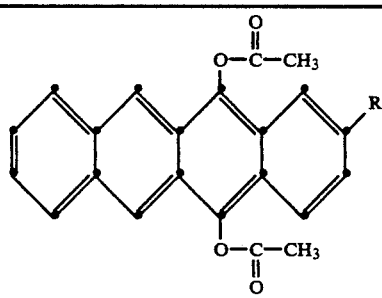

| Example No. | R | Yield (%) | Melting point (°C.) |
|---|---|---|---|
| 1 | —$OCH_3$ | 81 | 247–252 |
| 2 | —$OCH_2CH_3$ | 79 | 150–153 |
| 3 | —$OCH_2$—$CH(C_2H_5)(CH_2)_3CH_3$ | 71 | 130–135 |
| 4 | —O—n-$C_8H_{17}$ | 84 | 107–111 |
| 5 | —$OCH(CH_3)_2$ | 61 | 215–218 |
| 6 | —O—n-$C_{18}H_{37}$ | 49 | 155–157 |
| 7 | —$OCH_2CH=CH_2$ | 74 | 200–201 |
| 8 | —$OCH_2C\equiv CH$ | 59 | 213–215 |
| 9 | —$OCH_2CH_2OH$ | 47 | 189–193 |
| 10 | —$O(CH_2)_4OH$ | 36 | 181–183 |
| 11 | —$O(CH_2)_2O(CH_2)_2$—OH | 28 | 149–152 |
| 12 | —$SO_2CH_3$ | 69 | >250 |
| 13 | —$SCH_2CH_3$ | 77 | 130–135 |
| 14 | —S–⬡ | 79 | 145–150 |
| 15 | —$SO_2$–⬡ | 82 | >220 (decomposition) |
| 16 | F | 73 | 170–175 |
| 17 | —$C(CH_3)(COOC_2H_5)_2$ | 63 | 230 (decomposition) |
| 18 | —$CF_3$ | 91 | >250 |
| 19 | —$COOCH_3$ | 81 | 185–190 |
| 20 | —$COO(CH_2)_3CH_3$ | 73 | 195–196 |
| 21 | —$COO(CH_2)_7CH_3$ | 61 | 143–145 |
| 22 | —$COOCH_2CH(C_2H_5)(CH_2)_3CH_3$ | 45 | 149–150 | the polymer, if the chalcogenated tetracene is unsubstituted or contains small substituents (for example F, $CH_3$ or $CF_3$). Compositions of this type exhibit a high electrical conductivity. This can be improved further if a substituted tetrathiotetracene or tetraselenotetracene of the formula III which does not form such a network and which is present in the polymer matrix in finely divided form is concomitantly used, since substituted The corresponding 2-substituted naphthacene-5,12-diones of Examples 1–15 and 17 can be obtained by nucleophilic substitution of 2-fluoronaphthacene-5,12-dione.

2-(Trifluoromethyl)-naphthacene-5,12-dione 5.65 g (25 mmol) of 6-(trifluoromethyl)-1,4-naphthoquinone, 9.82 g (approx. 37 mmol) of 1,2-dibromobenzocyclobutene (containing a little 2-bromo-1-iodobenzocyclobutene as an impurity) and 100 ml of xylene are kept under reflux for 16 hours, using a water separator. The mixture is cooled and the precipitate is filtered off and washed with xylene. Yield 5.82 g (71%); melting poing 253°–254° C.

An analogous procedure is used in the preparation of 2,3-bis-(trifluoromethyl)-naphthacene-5,12-dione (yield 59%; melting point >280° C.); methyl 1-(trifluoromethyl)-naphthacene-5,12-dione-3-carboxylate (yield 60%; melting point 234°–235°) and methyl 2-ethoxynaphthacene-5,12-dione-3-carboxylate (yield 30%; melting point 192°–194° C.), which are used in the following examples 24–26.

Examples 23–27

1.65 mmol of 2-substituted naphthacene-5,12-dione, 5 ml of ethyl acetate, 4.96 mmol of potassium acetate and 3 ml of acetic anhydride are hydrogenated for 35 minutes at 20°–25° C., with the addition of 0.1 g of Pd/C (5%). The mixture is filtered and the residue is washed three times with $CH_2Cl_2$. The filtrates are concentrated, and the residue is recrystallized from $CH_2Cl_2$/pentane. The yields and melting points of the 5,12-diacetoxynaphthacenes obtained are indicated in Table 2.

TABLE 2

[Structure: naphthacene with O—CCH₃(=O) at 5 and 12 positions, with substituents R¹, R², R³]

| Example No. | R¹ | R² | R³ | Yield % | Melting point (°C.) |
|---|---|---|---|---|---|
| 23 | H | —OCH₂CH₃ | H | 70 | 149–153 |
| 24 | H | —CF₃ | —CF₃ | 76 | >250 |
| 25 | —CF₃ | H | —COOCH₃ | 18 | >280 |
| 26 | H | —OCH₂CH₃ | —COOC₂H₅ | 65 | 208–210 |
| 27[a] | H | —CH₃ | —CH₃ | 40 | >250 |

[a] 2,3-Dimethylnaphthacene-5,12-dione is obtained by subjecting 1,2-di-bromobenzocyclobutene to a condensation reaction with 6,7-dimethyl-naphthalene-1,4-dione with subsequent elimination of 2 HBr in situ.

Example 28

A solution of 400 ml of acetic anhydride and 11.1 g (0.04 mol) of tetrabutylammonium chloride is introduced into a cell divided by a D3 glass frit and equipped with a stainless steel cathode shaped in the form of a stirrer and a Pt anode. 3 g (0.67 mmol) of 2-(4-hydroxybutoxy)-naphthacene-5,12-dione are then added under nitrogen and electrolysis is carried out for 20 hours at a current of 20 mA. The solution in the cathode compartment is then poured into ice water and neutralized with saturated sodium carbonate solution. The precipitated product is filtered off and washed with water. Yield 3.8 g (90.5%) of 2-(4'-acetoxybutoxy)-5,12-diacetoxynaphthacene. Mass spectrum: $M^+ = 474$.

Elemental analysis: calculated: % C 70.87, % H 5.52, % O 23.60, found: % C 70.20, % H 5.60, % O 23.66.

Example 29

2-Ethoxy-5,12-bis-(trifluoroacetoxy)-naphthacene 2 g (6.62 mmol) of 2-ethoxynaphthacene-5,12-dione, 55 ml of trifluoroacetic anhydride, 2.7 g of sodium trifluoroacetate, 20 ml of ethyl acetate and 1.08 g (16.54 mmol) of zinc dust are stirred for 3 hours at 25°–30° C. The mixture is filtered and the residue is washed several times with tetrahydrofuran/$CH_2Cl_2$. The filtrates are evaporated and the residue is triturated with diethyl ether. The crystals are filtered off and recrystallized from toluene: yield 2.83 g (86%); melting point 165°–70° C.

Examples 30–36

1.83 mmol of substituted naphthacene-5,12-diacetate, 15.8 milliequivalents of $S_8$ and 0.026 mmol of p-toluenesulfonic acid in 100 ml of 1,2,4-trichlorobenzene are heated under a reflux, with a gentle flow of argon, in a 250 ml flask equipped with a reflux condenser and a gas inlet tube. The dark green solution is then evaporated under a high vacuum.

The crude product is chromatographed with $CCl_4$ over a silica gel flash column (240 g of silica gel, ∅0.7 cm). [The silica gel must be treated beforehand with $CCl_4$ containing 2% of triethylamine and must then be washed with pure $CCl_4$ until the eluate is again neutral.] The fractions of a dark green colour contain the purified 2-substituted 5,6,11,12-tetrathiotetracene. Spectral data and yields are shown in Table 3.

TABLE 3

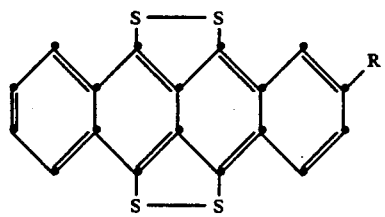

| Example No. | R | Mass spectrum (M⁺) | $\lambda_{max}$ (nm) in 1,2,4-tri-chlorobenzene | Yield (%) |
|---|---|---|---|---|
| 30 | —OC₂H₅ | 396 | 700 | 24[a] |
| 31 | —O-n-C₈H₁₇ | 480 | 699 | 50[b] |

TABLE 3-continued

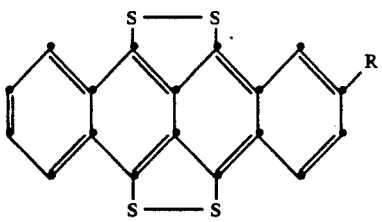

| Example No. | R | Mass spectrum (M+) | $\lambda_{max}$ (nm) in 1,2,4-tri-chlorobenzene | Yield (%) |
|---|---|---|---|---|
| 32 | —OCH$_2$CH(C$_2$H$_5$)(CH$_2$)$_3$CH$_3$ | 480 | 698 | 8[a] |
| 33 | —O-n-C$_{18}$H$_{37}$ | 620 | 698 | 50[a] |
| 34 | —C(CH$_3$)(COOC$_2$H$_5$)$_2$ | 524 | 704 | 10[a] |
| 35 | —COO(CH$_2$)$_3$CH$_3$ | 452 | 745 | 82% (crude) |
| 36 | —SC$_2$H$_5$ | 412 | 711 | 3%[a] |

[a] sublimed
[b] chromatographed

Example 37

251 mg (0.61 mmol) of 2-trifluoromethylnaphthacene-5,12-diacetate, 78 mg (2.43 milliequivalents) of S$_8$ and 2 mg (0.01 mmol) of p-toluenesulfonic acid in 35 ml of 1,2,4-trichlorobenzene are heated under reflux for 20 hours, with a gentle flow of argon, in a 100 ml flask equipped with a reflux condenser and a gas inlet tube. After cooling, the solvent is removed by evaporation under high vacuum (HV), the residue is boiled with hexane, and the black powder is filtered off and dried at 60° C. under HV. 203 mg (79%) of crude product are obtained.

This product is sublimed at 190° C. ($1.3 \times 10^{-4}$ mbar), and 67.5 mg (35.6%) of pure 2-trifluoromethyl-5,6-11,12-tetrathiotetracene are obtained (small black needles). Mass spectrum: M+=420. $\lambda_{max}$ (1,2,4-trichlorobenzene): 725, 665 and 484 nm.

Example 38

2,3-trifluoromethyl-5,6,11,12-tetrathiotetracene

The procedure followed is as in Example 37, and 2,3-trifluoromethylnaphthacene-5,12-diacetate is used. Yield: 75.6 mg (30%) after sublimation.

Mass spectrum: M+=488. $\lambda_{max}$ (1,2,4-trichlorobenzene): 755 nm.

B) Use examples

Example 39

Electrochromism 1 mg of 2,3-di-(trifluoromethyl)-5,6,11,12-tetrathiotetracene and 100 mg of LiClO$_4$, dissolved in 5 ml of acetone, are filled into the anode side, and a solution of 1 mg of 2,3-di-(trifluoromethyl)-5,6,11,12-tetrathiotetracene perchlorate (CT complex, for preparation see U.S. Pat. No. 3,634,336) and 100 mg of LiClO$_4$ in 5 ml of acetone are filled into the cathode side of an electrochromic cell consisting of a Teflon membrane and an anode and cathode of ITO glass, each at a distance of 0.5 mm. After a voltage of 2 volts has been applied, the colours change, in the course of a few seconds, from green to red-violet on the anode side and from red-violet to green on the cathode side. The original colours are obtained in both halves of the cell by reversing the polarity of the voltage. The same effect is observed if nitrobenzene or dimethylformamide is used as the solvent.

What is claimed is:

1. A compound of the formula I

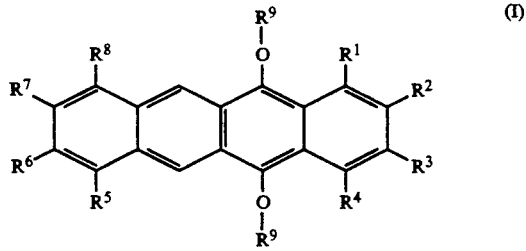

in which R$^1$ to R$^8$ independently of one another are H and at least one of R$^1$ to R$^8$ is —F, —Si(C$_1$-C$_4$alkyl)$_3$ or —COOR$^{10}$; or each pair of adjacent radicals of R$^1$ to R$^8$ is —CO—O—CO—; or at least one of R$^1$ to R$^8$ is C$_1$-C$_{20}$alkyl—(X)$_p$—, C$_2$-C$_{20}$alkenyl—(X)$_p$—, C$_2$-C$_{20}$alkynyl—(X)$_p$—, C$_3$-C$_8$cycloalkyl—(X)$_p$—, C$_1$-C$_{12}$alkyl—C$_3$-C$_8$cycloalkyl—(X)$_p$—, C$_3$-C$_8$—cycloalkyl—CH$_2$(X)$_p$—, C$_1$-C$_{12}$alkyl—C$_3$-C$_8$cycloalkyl—CH$_2$—(X)$_p$—, C$_6$-C$_{10}$aryl—X—, C$_7$-C$_{20}$alkaryl—X—, C$_7$-C$_{12}$aralkyl—(X)$_p$— or C$_8$-C$_{20}$alkaralkyl—(X)$_p$— or —Y—(C$_m$H$_{2m}$—O)$_n$—R$^{10}$ each of which is unsubstituted or substituted by —F, —OH, —CN, C$_1$-C$_{12}$alkoxy, C$_1$-C$_{12}$acyloxy or —COOR$^{10}$; R$^{10}$ is H or C$_1$-C$_{18}$alkyl, X is —O—, —S—, —SO— or —SO$_2$— and Y is —O— or —S—, and p is 0 or 1, m is a number from 2 to 6 and n is a number from 2 to 20; and R$^9$ is C$_1$-C$_4$acyl which is unsubstituted or substituted by -F, provided that when R$^1$-R$^6$ and R$^8$ are H and, R$^7$ is methyl, R$^9$ is not C$_2$-acyl.

2. A compound according to claim 1, in which R$^1$ to R$^8$ independently of one another are H and at least one of R$^1$ to R$^8$ is —F, —Si(CH$_3$)$_3$, —COO—(C$_1$-C$_{12}$alkyl), or at least one of R$^1$ to R$^8$ is C$_1$-C$_{18}$alkyl—(X)$_p$—, C$_2$-C$_{18}$alkenyl—(X)$_p$—, C$_2$-C$_{12}$alkynyl—(X)$_p$—, C$_6$-C$_{10}$aryl—X—, C$_7$-C$_{18}$alkaryl—X—, C$_7$-C$_{10}$aralkyl—(X)$_p$—, C$_8$-C$_{18}$alkaralkyl—(X)$_p$— or —Y—(C$_m$H$_{2m}$—O)$_n$—R$^{10}$ each of which is unsubstituted or substituted by —F, C$_1$-C$_6$alkoxy, C$_1$-C$_6$acyloxy or —COO—(C$_1$-C$_{12}$alkyl), R$^{10}$ is H or C$_1$-C$_6$alkyl, X is —O—, —S—, —SO— or —SO$_2$— and Y is —O— or —S—, m is 2 or 3 and n is a number from 2 to 12 and p is 0 or 1 and R$^9$ is acetyl which is unsubstituted or substituted by —F.

3. A compound according to claim 1, in which R$^4$, R$^5$ and R$^8$ are H.

4. A compound according to claim 1, in which $R^1$, $R^4$, $R^5$ and $R^8$ are H.

5. A compound according to claim 1, in which $R^2$, $R^3$ $R^2$ and $R^3$ are —F, —Si($C_1$-$C_4$alkyl)$_3$ or —COOR$^{10}$, and $R^1$ and $R^4$ to $R^8$ are H.

6. A compound according to claim 1, in which $R^6$, $R^7$ or $R^6$ and $R^7$ are —F, —Si($C_1$-$C_4$alkyl)$_3$ or —COOR$^{10}$, and $R^1$ to $R^5$ and $R^8$ are H.

7. A compound according to claim 1, in which $R^1$ is —CF$_3$ or —COO—($C_1$-$C_{12}$alkyl).

8. A compound according to claim 1, in which $R^1$ and $R^4$ to $R^8$ are H; $R^2$ is —F, —CF$_3$, —COO—($C_1$-$C_{18}$alkyl) or $C_1$-$C_{18}$alkyl—X— which is unsubstituted or substituted by —OH, —COO—($C_1$-$C_6$alkyl) or $C_1$-$C_6$acyloxy; —Y—($C_2C_2O$)$_n$—R$^{10}$ in which Y is —O— or —S—, R$^{10}$ is H or $C_1$-$C_6$alkyl and n is a number from 2 to 12; $C_2$-$C_{12}$alkenyl—CH$_2$—X—; $C_2$—$C_{12}$alkynyl—CH$_2$—X—; phenyl—X—; $C_1$-$C_{12}$—alkylphenyl—X—; benzyl—X—; or $C_1$-$C_{12}$alkylbenzyl—X— and $R_3$ H or independently is the same as $R_2$, and X is —O—, —S—, —SO— or —SO$_2$—.

* * * * *